(12) United States Patent
Moeckel et al.

(10) Patent No.: US 6,939,695 B2
(45) Date of Patent: Sep. 6, 2005

(54) NUCLEOTIDE SEQUENCES WHICH CODE FOR THE RPSL GENE

(75) Inventors: Bettina Moeckel, Duesseldorf (DE); Brigitte Bathe, Salzkotten (DE); Stefan Hans, Osnabrueck (DE); Caroline Kreutzer, Melle (DE); Thomas Hermann, Bielefeld (DE); Walter Pfefferle, Halle (DE); Michael Binder, Steinhagen (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/075,460

(22) Filed: Feb. 15, 2002

(65) Prior Publication Data

US 2002/0155557 A1 Oct. 24, 2002

(30) Foreign Application Priority Data

Feb. 16, 2001 (DE) .......................... 101 07 230
Dec. 19, 2001 (DE) .......................... 101 62 386

(51) Int. Cl.$^7$ .......................... C12P 13/04; C07H 21/04
(52) U.S. Cl. .......................... 435/115; 435/106; 435/183; 435/193; 435/252.32; 435/320.1; 435/91.1; 536/23.1; 536/23.2; 536/23.7; 530/350
(58) Field of Search .......................... 435/106, 115, 435/91.1, 183, 193, 252.32, 320.1, 252.3; 536/23.1, 23.2, 23.7; 530/350

(56) References Cited

FOREIGN PATENT DOCUMENTS

| EP | 1 108 790 | 6/2001 |
|---|---|---|
| WO | WO 93/22454 | 11/1993 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
U.S. Appl. No. 10/801,847, filed Mar. 17, 2004, Hermann, et al.
U.S. Appl. No. 10/075,460, filed Feb. 15, 2002, Moeckel, et al.

J. Nair, et al., Nucleic Acids Research, vol. 21, No. 4, XP–001109036, p. 1039, "Nucleotide Sequence Analysis of the Ribosomal S12 Gene of Mycobacterium Intracellulare", 1993.
M. Marchetti, et al., Database Swall, Online, AN Q9R787, XP–002217042, 1 page, "Mutations Affecting the Colonizing–Potential of Helicobacter Pylori Map Within the CAG Pathogenicity Island", May 1, 2000 (abstract only).
B. J. Elkmanns, et al., Antonia van Leeuwenhoek, vol. 64, No. 2, XP–000918559, pp. 145–163, "Molecular Aspects of Lysine, Threonine, and Isoleucine Biosynthesis in Corynebacterium Glutamicum", 1993.
R. Kraemar, Journal of Biotechnology, vol. 45, No. 1, XP–0004036833, pp. 1–21, "Genetic and Physiological Approaches for the Production of Amino Acids", Feb. 12, 1996.
L. Eggeling, et al., Applied Microbiology and Biotechnology, vol. 52, XP–000979507, pp. 146–153, "L–Glutamate and L–Lysine: Traditional Products with Impetuous Developments", Aug. 1999.

* cited by examiner

Primary Examiner—Richard Hutson
(74) Attorney, Agent, or Firm—Oblon, Spivak, McClelland, Maier & Neustadt, P.C.

(57) ABSTRACT

An isolated polynucleotide comprising a polynucleotide sequence chosen from the group consisting of
  a) polynucleotide which is identical to the extent of at least 70% to a polynucleotide which codes for a polypeptide which comprises the amino acid sequence of SEQ ID No. 2,
  b) polynucleotide which codes for a polypeptide which comprises an amino acid sequence which is identical to the extent of at least 70% to the amino acid sequence of SEQ ID No. 2,
  c) polynucleotide which is complementary to the polynucleotides of a) or b), and
  d) polynucleotide comprising at least 15 successive nucleotides of the polynucleotide sequence of a), b) or c),
and a process for the fermentative preparation of L–amino acids using coryneform bacteria in which at least the rpsL gene is present in enhanced form, as well as the use of polynucleotides which comprise the sequences according to the invention as hybridization probes.

43 Claims, 1 Drawing Sheet

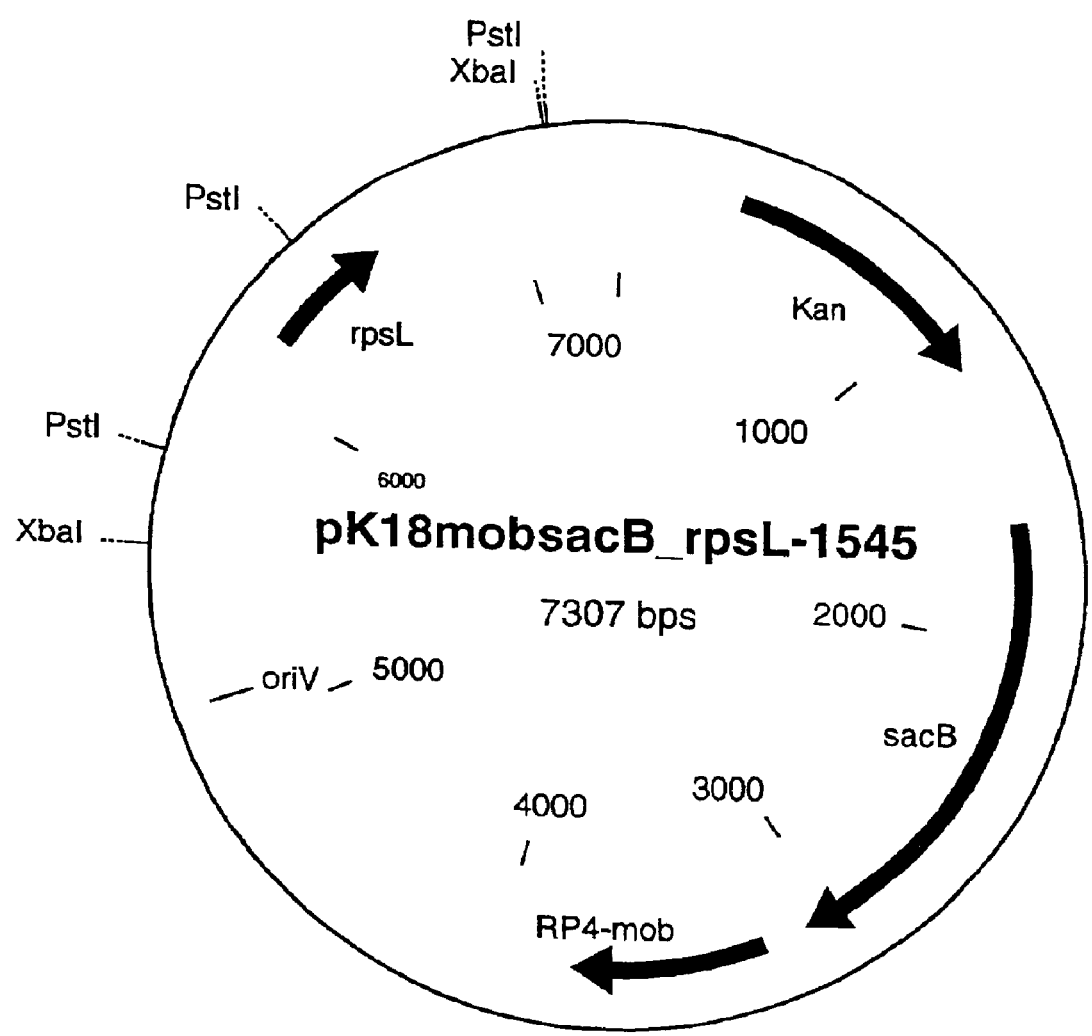

US 6,939,695 B2

NUCLEOTIDE SEQUENCES WHICH CODE FOR THE RPSL GENE

BACKGROUND OF THE INVENTION

1. Field of the Invention

The present invention provides nucleotide sequences from coryneform bacteria which code for the rpsL gene and a process for the fermentative preparation of amino acids using bacteria in which the rpsL gene is enhanced.

2. Background of the Invention

L-Amino acids, in particular L-lysine, are used in human medicine and in the pharmaceuticals industry, in the foodstuffs industry, and, very particularly, in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and produce amino acids are obtained in this manner.

Methods of the recombinant DNA technique have also been employed for some years for improving the strain of *Corynebacterium* strains which produce L-amino acid, by amplifying individual amino acid biosynthesis genes and investigating the effect on the amino acid production. However, there is a continuing need for new methods of producing L-amino acids.

SUMMARY OF THE INVENTION

It is an object of the present invention to provide new methods for an improved fermentative preparation of amino acids.

The present invention is based on the discovery that bacteria in which the rpsL gene is enhanced can be used to fementatively produce amino acids.

Accordingly, the invention provides an isolated polynucleotide from coryneform bacteria, comprising a polynucleotide sequence which codes for the rpsL gene chosen from the group consisting of a
  a) polynucleotide which is identical to the extent of at least 70% to a polynucleotide which codes for a polypeptide which comprises the amino acid sequence of SEQ ID No. 2,
  b) polynucleotide which codes for a polypeptide which comprises an amino acid sequence which is identical to the extent of at least 70% to the amino acid sequence of SEQ ID No. 2,
  c) polynucleotide which is complementary to the polynucleotides of a) or b), and
  d) polynucleotide comprising at least 15 successive nucleotides of the polynucleotide sequence of a), b) or c),
the polypeptide preferably having the activity of the ribosomal protein S12.

The present invention also provides the above-mentioned polynucleotide, this preferably being a DNA which is capable of replication, comprising:

(i) the nucleotide sequence shown in SEQ ID no. 1, or
  (ii) at least one sequence which corresponds to sequence (i) within the range of the degeneration of the genetic code, or
  (iii) at least one sequence which hybridizes with the sequence complementary to sequence (i) or (ii), and optionally
  (iv) sense mutations of neutral function in (i) which do not modify the activity of the protein/polypeptide In addition, the present invention also provides polynucleotides chosen from the group consisting of
  a) polynucleotides comprising at least 15 successive nucleotides chosen from the nucleotide sequence of SEQ ID No. 1 between positions 1 and 499,
  b) polynucleotides comprising at least 15 successive nucleotides chosen from the nucleotide sequence of SEQ ID No. 1 between positions 500 and 883,
  c) polynucleotides comprising at least 15 successive nucleotides chosen from the nucleotide sequence of SEQ ID No. 1 between positions 884 and 1775.

The present invention also provides
  a polynucleotide, in particular DNA, which is capable of replication and comprises the nucleotide sequence as shown in SEQ ID No. 1;
  a polynucleotide which codes for a polypeptide which comprises the amino acid sequence as shown in SEQ ID No. 2;
  a vector containing the polynucleotide according to the invention, in particular a shuttle vector or plasmid vector, and
  coryneform bacteria which contain the vector or in which the rpsL gene is enhanced.

In addition, the present invention also provides the *Corynebacterium glutamicum* strain DM1545 deposited as DSM 13992 at the Deutsche Sammlung für Mikroorganismen und Zellkulturen (DSMZ, German Collection of Microorganisms and Cell Cultures, Braunschweig, Germany).

The present invention also provides a process for the fermentative preparation of an L-amino acid, comprising:
  a) fermenting coryneform bacteria which produce the L-amino acid and in which at least the rpsL gene or nucleotide sequences which code for it are enhanced,
  b) concentrating the L-amino acid in the medium or in the cells of the bacteria, and
  c) isolating the L-amino acid.

The present invention also provides a process for discovering RNA, cDNA and DNA in order to isolate nucleic acids or polynucleotides or genes which code for the ribosomal protein S12 or have a high similarity with the sequence of the rpsL gene, which comprises employing the polynucleotide comprising the polynucleotide sequences as claimed in claim 1 as a hybridization probe.

The present invention additionally provides a process for identifying a nucleic acid which codes for the ribosomal protein S12 or have a high similarity with the sequence of the rpsL gene, comprising:
  contacting a sample with the polynucleotide sequence as claimed in claim 1 under conditions under hybridization conditions such that the polynucleotide sequence as claimed in claim 1 hybridizes with said nucleic acid when said nucleic acid is present in the sample.

Further, the present invention additionally provides:
  a DNA which originates from coryneform bacteria and codes for ribosomal S12 proteins, wherein the associated amino acid sequences between positions 38 to 48 in SEQ ID No. 2 are modified by amino acid exchange;

a DNA which originates from coryneform bacteria and codes for ribosomal S12 proteins, wherein the associated amino acid sequences at position 43 in SEQ ID No. 2 contain any other proteinogenic amino acid excluding L-lysine; and a DNA which originates from coryneform bacteria and codes for ribosomal S12 proteins, wherein the associated amino acid sequences at position 43 in SEQ ID No. 2 contain L-histidine or L-arginine.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID No. 1 or a fragment thereof, and isolation of the polynucleotide sequence mentioned.

Polynucleotides which comprise the sequences according to the invention are suitable as hybridization probes for RNA, cDNA and DNA, in order to isolate, in the full length, nucleic acids or polynucleotides or genes which code for the ribosomal protein S12 or to isolate those nucleic acids or polynucleotides or genes which have a high similarity with the sequence of the rpsL gene. They can also be applied as a probe on so-called "arrays", micro arrays" or "DNA chips" in order to detect and determine the corresponding polynucleotides or sequences derived therefrom, such as e.g. RNA or cDNA.

BRIEF DESCRIPTION OF THE FIGURES

A more complete appreciation of the invention and many of the attendant advantages thereof will be readily obtained as the same becomes better understood by reference to the following Figure in conjunction with the detailed description below.

FIG. 1: plasmid pK18mobsacB_rpsL-1545.

DETAILED DESCRIPTION OF THE INVENTION

Where L-amino acids or amino acids are mentioned herein, this means one or more amino acid, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

When L-lysine or lysine are mentioned herein, not only the bases but also the salts, such as e.g. lysine monohydrochloride or lysine sulfate, are encompassed term by this.

Polynucleotides which comprise the sequences according to the invention are furthermore suitable as primers with the aid of which DNA of genes which code for the ribosomal protein S12 can be prepared by the polymerase chain reaction (PCR). Such oligonucleotides which serve as probes or primers comprise at least 25, 26, 27, 28, 29 or 30, preferably at least 20, 21, 22, 23 or 24, very particularly preferably at least 15, 16, 17, 18 or 19 successive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment. "Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least in particular 70% to 80%, preferably at least 81% to 85%, particularly preferably at least 86% to 90%, and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the ribosomal protein S12 and also those which are at least 70% to 80%, preferably at least 81% to 85%, particularly preferably at least 86% to 90%, and very particularly preferably at least 91%, 93%, 95%, 97% or 99% identical to the polypeptide according to SEQ ID No. 2 and have the activity described above.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences, preferably endogenous, which code for the rpsL gene are enhanced, in particular over-expressed.

The term "enhancement" in this connection describes the increase in the intracellular activity of one or more enzymes or proteins in a microorganism which are coded by the corresponding DNA, for example by increasing the number of copies of the gene or genes, using a potent promoter or using a gene or allele which codes for a corresponding enzyme or protein with a high activity, and optionally combining these measures. By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The microorganisms provided by present invention can produce L-amino acids from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among those skilled in the art for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-amino acid-producing mutants or strains prepared therefrom, such as, for example, the L-lysine-producing strains

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM5715 and
*Corynebacterium glutamicum* DSM12866.

The new rpsL gene from *C. glutamicum* which codes for the ribosomal protein S12 has been isolated as described herein.

To isolate the rpsL gene or also other genes of *C. glutamicum*, a gene library of this microorganism is first established in *Escherichia coli* (*E. coli*). The establishment of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was established with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)).

To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)). The new DNA sequence of *C. glutamicum* which codes for the rpsL gene and which, as SEQ ID No. 1, is a constituent of the present invention has been found. The amino acid sequence of the corresponding protein has furthermore been derived from the present DNA sequence by the methods described above. The resulting amino acid sequence of the rpsL gene product is shown in SEQ ID No. 2. It is known that enzymes endogenous in the host can split off the N-terminal amino acid methionine or formylmethionine of the protein formed. Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. Such mutations are also called, inter alia, neutral substitutions. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approximately 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approximately 50° C.–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50° C. to 68° C. in steps of approximately 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide synthesis: A Practical Approach (IRL Press, Oxford, UK, 1984) and in Newton and Graham: PCR (Spektrum Akademischer Verlag, Heidelberg, Germany, 1994). It has been found that coryneform bacteria produce amino acids in an improved manner after enhancement of the rpsL gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative amino acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification 0 472 869, in U.S. Pat. No. 4,601,893, in Schwarzer and Pühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the rpsL gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically E. coli), but not in C. glutamicum. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega Corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al., 1986, Gene 41: 337–342). The plasmid vector which contains the gene to be amplified is then transferred into the desired strain of C. glutamicum by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

It has furthermore been found that amino acid exchanges in the section between position 38 to 48 of the amino acid sequence of the ribosomal protein S12 shown in SEQ ID No. 2 improve the lysine production of coryneform bacteria.

Preferably, L-lysine at position 43 is exchanged for any other proteinogenic amino acid excluding L-lysine, exchange for L-histidine or L-arginine being preferred. Exchange for L-arginine is very particularly preferred.

The base sequence of the allele rpsL-1545 contained in strain DM1545 is shown in SEQ ID No. 3. The rpsL-1545 allele codes for a protein, the amino acid sequence of which is shown in SEQ ID No. 4. The protein contains L-arginine at position 43. The DNA sequence of the rpsL-1545 allele (SEQ ID No. 3) contains the base guanine at position 128 of the coding region (CDS), which corresponds to position 627 in the sequence shown in SEQ ID No. 3. The DNA sequence of the wild-type gene (SEQ ID No. 1) contains the base adenine at this position For mutagenesis, conventional mutagenesis processes can be used, using mutagenic substances such as, for example, N-methyl-N'-nitro-N-nitrosoguanidine or ultraviolet light. In vitro methods, such as, for example, a treatment with hydroxylamine (Miller, J. H.: A Short Course in Bacterial Genetics. A Laboratory Manual and Handbook for Escherichia coli and Related Bacteria, Cold Spring Harbor Laboratory Press, Cold Spring Harbor, 1992) or mutagenic oligonucleotides (T. A. Brown: Gentechnologie für Einsteiger [Genetic Engineering for Beginners], Spektrum Akademischer Verlag, Heidelberg, 1993) or the polymerase chain reaction (PCR), such as is described in the handbook by Newton and Graham (PCR, Spektrum Akademischer Verlag, Heidelberg, 1994), can furthermore be used for the mutagenesis.

The rpsL allele according to the invention can also be transferred into suitable strains, inter alia, by the method of gene replacement, such as is described by Schwarzer and Pühler (Bio/Technology 9, 84–87 (1991)) or Peters-Wendisch et al. (Microbiology 144, 915–927 (1998)). The corresponding rpsL allele is cloned here in a vector which is not replicative for C. glutamicum, such as, for example, pK18mobsacB or pK19mobsacB (Jäger et al., Journal of Bacteriology 174: 5462–65 (1992)) or pCR®Blunt (Invitrogen, Groningen, Holland; Bernard et al., Journal of Molecular Biology, 234: 534–541 (1993)) and this is then transferred into the desired host of C. glutamicum by transormation or conjugation. After homologous recombination by means of a first "cross-over" event which effects integration and a suitable second "cross-over" event which effects excision in the target gene or in the target sequence, the incorporation of the mutation is achieved.

In addition, it may be advantageous for the production of L-amino acids to enhance, in particular over-express, one or more enzymes of the particular biosynthesis pathway, of glycolysis, of anaplerosis, of the citric acid cycle, of the pentose phosphate cycle, of amino acid export and optionally regulatory proteins, in addition to the rpsL gene. The use of endogenous genes is in general preferred.

"Endogenous genes" or "endogenous nucleotide sequences" are understood as meaning the genes or nucleotide sequences and alleles thereof present in the population of a species.

Thus, for the preparation of L-lysine, in addition to enhancement of the rpsL gene, one or more genes chosen from the group consisting of the dapA gene which codes for dihydrodipicolinate synthase (EP-B 0 197 335), the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the zwf gene which codes for glucose 6-phosphate dehydrogenase (JP-A-09224661), the pyc gene which codes for pyruvate carboxylase (DE-A-198 31 609), the mqo gene which codes for malate-quinone oxidoreductase (Molenaar et al., European Journal of Biochemistry 254, 395–403 (1998)), the lysC gene which codes for a feed-back resistant aspartate kinase (Kalinowski et al. (1990), Molecular Microbiology 5(5), 1197–204 (1991)), the lysE gene which codes for the lysine export protein (DE-A-195 48 222), the zwa1 gene which codes for the Zwa1 protein (DE: 19959328.0, DSM 13115), and the rpoB gene which codes for the β-subunit of RNA polymerase B, shown in SEQ ID No. 5 and 6 can be enhanced, in particular over-expressed.

The term "attenuation" in this context describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

It may furthermore be advantageous for the production of L-amino acids, in addition to the enhancement of the rpsL gene, for one or more genes chosen from the group consisting of:

the pck gene which codes for phosphoenol pyruvate carboxykinase (DE 199 50 409.1; DSM 13047), the pgi gene which codes for glucose 6-phosphate isomerase (US 09/396,478; DSM 12969), the poxB gene which codes for pyruvate oxidase (DE: 1995 1975.7; DSM 13114), the zwa2 gene which codes for the Zwa2 protein (DE: 19959327.2, DSM 13113) to be attenuated, in particular for the expression thereof to be reduced.

In addition to enhancement of the rpsL gene it may furthermore be advantageous for the production of amino acids to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of amino acids. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)). The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e. g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are well known to those skilled in the art. The analysis can thus be carried out, for example, as described by Spackman et al.

(Analytical Chemistry, 30, (1958), 1190) by ion exchange chromatography with subsequent ninhydrin derivation, or it can be carried out by reversed phase HPLC, for example as described by Lindroth et al. (Analytical Chemistry (1979) 51: 1167–1174).

A pure culture of the *Corynebacterium glutamicum* strain DM1545 was deposited on 16 Jan. 2001 at the Deutsche Sammlung für Mikroorganismen und Zellkulturen (DSMZ= German Collection of Microorganisms and Cell Cultures, Braunschweig, Germany) in accordance with the Budapest Treaty as DSM 13992.

The process according to the invention is used for the fermentative preparation of amino acids, in particular L-lysine.

EXAMPLES

Having generally described this invention, a further understanding can be obtained by reference to certain specific examples which are provided herein for purposes of illustration only and are not intended to be limiting unless otherwise specified.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbor Laboratory Press, Cold Spring Harbor, N.Y., USA). Methods for transformation of *Escherichia coli* are also described in this handbook.

The composition of the usual nutrient media, such as LB or TY medium, can also be found in Sambrook et al. cited above.

Example 1

Preparation of a Genomic Cosmid Gene Library from *Corynebacterium glutamicum* ATCC 13032

Chromosomal DNA from *Corynebacterium glutamicum* ATCC 13032 is isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments are dephosphorylated with shrimp alkaline phosphatase (Roche Diagnostics GmbH, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) is cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA is then cleaved with the restriction enzyme BamHI (Amersham Pharmacia, Freiburg, Germany, Product Description BamHI, Code no. 27-0868-04). The cosmid DNA treated in this manner is mixed with the treated ATCC13032 DNA and the batch is treated with T4 DNA ligase (Amersham Pharmacia, Freiburg, Germany, Product Description T4-DNA-Ligase, Code no.27-0870-04). The ligation mixture is then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells are taken up in 10 mM $MgSO_4$ and mixed with an aliquot of the phage suspension. The infection and titering of the cosmid library are carried out as described by Sambrook et al. (1989, Molecular Cloning: A Laboratory Manual, Cold Spring Harbor), the cells being plated out on LB agar (Lennox, 1955, Virology, 1:190) with 100 mg/l ampicillin. After incubation overnight at 37° C., recombinant individual clones are selected.

Example 2

Isolation and Sequencing of the rpsL Gene

The cosmid DNA of an individual colony is isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments are dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp are isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), is cleaved with the restriction enzyme BamHI (Amersham Pharmacia, Freiburg, Germany, Product Description BamHI, Product No. 27-0868-04). The ligation of the cosmid fragments in the sequencing vector pZero-1 is carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture is then electroporated (Tauch et al. 1994, FEMS Microbiol Letters, 123:343–7) into the *E. coli* strain DH5αMCR (Grant, 1990, Proceedings of the National Academy of Sciences U.S.A., 87:4645–4649) and plated out on LB agar (Lennox, 1955, Virology, 1:190) with 50 mg/l zeocin.

The plasmid preparation of the recombinant clones is carried out with a Biorobot 9600 (Product No. 900200, Qiagen, Hilden, Germany). The sequencing is carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) is used. The separation by gel electrophoresis and analysis of the sequencing reaction are carried out in a "Rotiphoresis NF Acrylamide/Bisacrylamide" Gel (29: 1) (Product No. A124.1, Roth, Karlsruhe, Germany) with the "ABI Prism 377" sequencer from PE Applied Biosystems (Weiterstadt, Germany).

The raw sequence data obtained are then processed using the Staden program package (1986, Nucleic Acids Research, 14:217–231) version 97-0. The individual sequences of the pZero1 derivatives are assembled to a continuous contig. The computer-assisted coding region analysis is prepared with the XNIP program (Staden, 1986, Nucleic Acids Research 14:217–231).

The resulting nucleotide sequence is shown in SEQ ID No. 1. Analysis of the nucleotide sequence shows an open reading frame of 383 base pairs, which is called the rpsL gene. The rspL gene codes for a protein of 127 amino acids.

The DNA section lying upstream of SEQ ID No. 1 was identified in the same way, this section being shown in SEQ ID No. 7. The rpsL gene region extended by SEQ ID No. 7 is shown in SEQ ID No. 8.

Example 3

Amplification and Sequencing of the DNA of the rpsL Allele of Strain DM1545

The *Corynebacterium glutamicum* strain DM1545 was prepared by multiple, non-directed mutagenesis, selection and mutant selection from *C. glutamicum* ATCC13032. The strain is methionine-sensitive.

From the strain DM1545, chromosomal DNA is isolated by conventional methods (Eikmanns et al., Microbiology 140: 1817–1828 (1994)). With the aid of the polymerase chain reaction, a DNA section which carries the rpsL gene or allele is amplified. On the basis of the sequence of the rpsL gene known for *C. glutamicum* from example 2, the following primer oligonucleotides are chosen for the PCR:
rpsL-1 (SEQ ID No. 10):
5' cag ctc tac aag agt gtc ta 3'
rpsL-2 (SEQ ID No. 11):
5' tgg tcg tgg tct tac cag ca 3'

The primers shown are synthesized by MWG Biotech (Ebersberg, Germany) and the PCR reaction is carried out by the standard PCR method of Innis et al. (PCR Protocols. A Guide to Methods and Applications, 1990, Academic Press). The primers allow amplification of a DNA section of approx. 1.78 kb in length, which carries the rpsL allele.

The amplified DNA fragment of approx. 1.78 kb in length which carries the rpsL allele of the strain DM1545 is identified by electrophoresis in a 0.8% agarose gel, isolated from the gel and purified by conventional methods (QIAquick Gel Extraction Kit, Qiagen, Hilden).

The nucleotide sequence of the amplified DNA fragment or PCR product is determined by sequencing by MWG Biotech (Ebersberg, Germany). The sequence of the PCR product is shown in SEQ ID No. 3. The amino acid sequence of the associated ribosomal protein S12 resulting with the aid of the Patentin program is shown in SEQ ID No. 4.

At position 128 of the nucleotide sequence of the coding region of the rpsL allele of strain DM1545, that is to say at position 627 of the nucleotide sequence shown in SEQ ID No. 3, is the base guanine. At the corresponding position of the wild-type gene is the base adenine (SEQ ID No. 1).

At position 43 of the amino acid sequence of the ribosomal protein S12 of strain DM1545 is the amino acid arginine (SEQ ID No. 4). At the corresponding position of the wild-type protein is the amino acid lysine (SEQ ID No. 2).

Example 4

Replacement of the rpsL Wild-type Gene of Strain DSM5715 by the rpsL-1545 Allele

4.1 Isolation of a DNA Fragment which Carries the rpsL-1545 Allele

From the strain DM1545, chromosomal DNA is isolated by the conventional methods (Eikmanns et al., Microbiology 140: 1817–1828 (1994)). A DNA section which carries the rpsL-1545 allele which contains the base guanine at position 128 of the coding region (CDS) instead of the bases adenine contained at this position in the wild-type gene is amplified with the aid of the polymerase chain reaction. On the basis of the sequence of the rpsL gene known for *C. glutamicum* from example 2, the following primer oligonucleotides are chosen for the polymerase chain reaction:

rpsL_XL-A1 (SEQ ID No. 12):
5' ga tct aga-ggt tgc cgg taa tcc tgt tg 3'
rpsL_XL-E 1 (SEQ ID No. 13):
5' ga tct aga-cgc agg ctg cca gct tat tc 3'

The primers shown are synthesized by MWG Biotech (Ebersberg, Germany) and the PCR reaction is carried out by the standard PCR method of Innis et al. (PCR Protocols. A Guide to Methods and Applications, 1990, Academic Press). The primers allow amplification of a DNA section approx. 1.59 kb in length which carries the rpsL-1545 allele (SEQ ID No. 9). The primers moreover contain the sequence for a cleavage site of the restriction endonuclease XbaI, which is marked by underlining in the nucleotide sequence shown above. The amplified DNA fragment of approx. 1.59 kb in length which carries the rpsL-1545 allele is cleaved with the restriction endonuclease XbaI, identified by electrophoresis in a 0.8% agarose gel and then isolated from the gel and purified by conventional methods (QIAquick Gel Extraction Kit, Qiagen, Hilden).

4.2 Construction of the Exchange Vector pK18mobsacB_rpsL- 1545

The approximately 1.58 kb long DNA fragment cleaved with the restriction endonuclease XbaI, which contains the rpsL- 1545 allele and is described in example 4.1, is incorporated by means of replacement mutagenesis with the aid of the sacB system described by Schäfer et al. (Gene, 14, 69–73 (1994)) into chromosome of the *C. glutamicum* strain DSM5715. This system enables preparation and selection of allele exchanges which take place by homologous recombination.

The mobilizable cloning vector pK18mobsacB is digested with the restriction enzyme XbaI and the ends are dephosphorylated with alkaline phosphatase (Alkaline Phosphatase, Boehringer Mannheim, Germany). The vector prepared in this way is mixed with the rpsL-1545 fragment approx. 1.58 kb in size and the mixture is treated with T4 DNA ligase (Amersham-Pharmacia, Freiburg, Germany).

The *E. coli* strain S17-1 (Simon et al., Bio/Technologie 1: 784–791, 1993) is then transformed with the ligation batch (Hanahan, In. DNA cloning. A Practical Approach. Vol. 1, ILR-Press, Cold Spring Harbor, N.Y., 1989). Selection of plasmid-carrying cells is made by plating out the transformation batch on LB agar (Sambrook et al., Molecular Cloning: A Laboratory Manual. $2^{nd}$ Ed., Cold Spring Harbor, N.Y., 1989), which was supplemented with 25 mg/l kanamycin.

Plasmid DNA is isolated from a transformant with the aid of the QIAprep Spin Miniprep Kit from Qiagen and checked by restriction cleavage with the enzyme PstI and subsequent agarose gel electrophoresis. The plasmid is called pK18mobsacB_rpsL-1545 and is shown in FIG. 1.

4.3 Integration of the Vector pK18mobsacB_rpsL-1545 in DSM5715 and Allele Exchange The vector pK18mobsacB_rpsL-1545 mentioned in example 4.2 is transferred by conjugation by the protocol of Schäfer et al. (Journal of Microbiology 172: 1663–1666 (1990)) into *C. glutamicum* strain DSM5715. The vector cannot replicate independently in DSM5715 and is retained in the cell only if it is present integrated in the chromosome as the consequence of a recombination event. Selection of transconjugants, i.e. clones with integrated pK18mobsacB_rpsL-1545, is made by plating out the conjugation batch on LB agar (Sambrook et al., Molecular Cloning: A Laboratory Manual. $2^{nd}$ Ed., Cold Spring Harbor, N.Y., 1989), which is supplemented with 15 mg/l kanamycin and 50 mg/l nalidixic acid. Kanamycin-resistant transconjugants are plated out on LB agar plates with 25 mg/l kanamycin and incubated for 24 hours at 33° C. A kanamycin-resistant transconjugant is called DSM5715::pK18mobsacB_rpsL-1545. By integration of the vector, in addition to the rpsL wild-type gene it carries the rpsL-1545 allele in the chromosome. For selection of mutants in which excision of the plasmid has taken place as a consequence of a second recombination event, cells of the strain DSM5715::pK18mobsacB_rpsL-1545 are cultured for 30 hours unselectively in LB liquid medium and then plated out on LB agar with 10% sucrose and incubated for 16 hours.

The plasmid pK18mobsacB_rpsL-1545, like the starting plasmid pK18mobsacB, contains, in addition to the kanamycin resistance gene, a copy of the sacB gene which codes for levan sucrase from *Bacillus subtilis*. The expression which can be induced by sucrose leads to the formation of levan sucrase, which catalyses the synthesis of the product levan, which is toxic to *C. glutamicum*. Only those clones in which the integrated pK18mobsacB_rpsL-1545 has excised as the consequence of a second recombination event therefore grow on LB agar. Depending on the position of the second recombination event with respect to the mutation site, allele exchange or incorporation of the mutation takes place with the excision, or the original copy remains in the chromosome of the host.

Approximately 40 to 50 colonies are tested for the phenotype "growth in the presence of sucrose" and "non-growth in the presence of kanamycin". In 4 colonies which show the phenotype "growth in the presence of sucrose" and "non-growth in the presence of kanamycin", a region of the rpsL gene spanning the rpsL-1545 mutation is sequenced, starting from the sequencing primer rL_1 (SEQ ID No. 14), by GATC Biotech AG (Constance, Germany) to demonstrate that the mutation of the rpsL-1545 allele is present in the chromosome. The primer rL-1 used is synthesized for this by GATC:

rL_1 (SEQ ID No. 14):

5' atg agg ttg tcc gtg aca tg 3'

A clone which contains the base guanine at position 128 of the cording region (CDS) of the rpsL gene and thus has the rpsL-1545 allele was identified in this manner. This clone was denoted strain DSM5715_rpsL-1545.

Example 5

Preparation of Lysine

The *C. glutamicum* strains DSM5715::pK18mobsacB_rpsL-1545 and DSM5715rpsL-1545 obtained in example 4 are cultured in a nutrient medium suitable for the production of lysine and the lysine content in the culture supernatant is determined.

For this, the strains are first incubated on an agar plate for 24 hours at 33° C. Starting from this agar plate culture, in each case a preculture is seeded (10 ml medium in a 100 ml conical flask). The medium MM is used as the medium for the precultures. The precultures are incubated for 24 hours at 33° C. at 240 rpm on a shaking machine. In each case a main culture is seeded from these precultures such that the initial OD (660 nm) of the main cultures is 0.1. The Medium MM is also used for the main cultures.

|  | Medium MM |
|---|---|
| CSL | 5 g/l |
| MOPS | 20 g/l |
| Glucose (autoclaved separately) | 50 g/l |

-continued

|  | Medium MM |
|---|---|
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL (corn steep liquor), MOPS (morpholinopropanesulfonic acid) and the salt solution are brought to pH 7 with aqueous ammonia and autoclaved. The sterile substrate and vitamin solutions, as well as the $CaCO_3$ autoclaved in the dry state, are then added. Culturing is carried out in a 10 ml volume in a 100 ml conical flask with baffles. Culturing is carried out at 33° C. and 80% atmospheric humidity.

After 72 hours, the OD is determined at a measurement wavelength of 660 nm with a Biomek 1000 (Beckmann Instruments GmbH, Munich). The amount of lysine formed is determined with an amino acid analyzer from Eppendorf-BioTronik (Hamburg, Germany) by ion exchange chromatography and post-column derivation with ninhydrin detection.

The result of the experiment is shown in table 1.

TABLE 1

| Strain | OD (660 nm) | Lysine HCl |
|---|---|---|
| DSM5715 | 8.2 | 13.57 |
| DSM5715::pK18mobsacB_rpsL-1545 | 9.2 | 15.28 |
| DSM5715rpsL-1545 | 7.9 | 14.74 |

Obviously, numerous modifications and variations of the present invention are possible in light of the above teachings. It is therefore to be understood that within the scope of the appended claims, the invention may be practiced otherwise than as specifically described herein.

All publications cited above are incorporated herein by reference.

This application is based on German patent application serial Nos. 101 07 230.9, filed on Feb. 16, 2001; and German patent application serial No. 101 62 386.0, filed Dec. 19, 2001, both of which are incorporated herein by reference in their entirety.

What is claimed is:

1. An isolated polynucleotide comprising a polynucleotide sequence selected from the group consisting of:
   a) a polynucleotide which is at least 95% identical to a polynucleotide which encodes SEQ ID NO: 4 and which encodes a polypeptide which increases lysine production in corynebacteria, and
   b) a polynucleotide which encodes a polypeptide which is at least 95% identical to SEQ ID NO: 4 and which encodes a polypeptide which increases lysine production in corynebacteria,
   wherein the polynucleotide of a) and b) encodes a polypeptide which comprises an arginine residue at the position corresponding to position 43 of SEQ ID NO: 4.

2. The polynucleotide of claim 1, which is at least 95% identical to a polynucleotide which encodes SEQ ID NO: 4 and which encodes a polypeptide which increases lysine production in corynebacteria.

3. The polynucleotide of claim 1, which is at least 97% identical to a polynucleotide which encodes SEQ ID NO: 4.

4. The polynucleotide of claim 1, which is at least 95% identical to SEQ ID NO: 3.

5. The polynucleotide of claim 1, which is at least 97% identical to SEQ ID NO: 3.

6. An isolated polynucleotide which hybridizes to SEQ ID NO: 3 under stringent conditions and which encodes a polypeptide which increases lysine production in corynebactoria,
   wherein stringent conditions comprise hybridization in 5× SSC and washing in 2× SSC at a temperature ranging from 50° C. to 68° C.,
   wherein said encoded polypeptide comprises an arginine residue at the position corresponding to position 43 of SEQ ID NO: 4.

7. The polynucleotide of claim 6, which comprises SEQ ID NO: 3.

8. The polynucleotide of claim 1, which is RNA.

9. The polynucleotide of claim 1, which comprises SEQ ID NO: 3, or a fragment of SEQ ID NO: 3, which encodes a polypeptide which increases lysine production in corynebacteria.

10. The polynucleotide of claim 1, which consists of SEQ ID NO:3.

11. The polynucleotide of claim 1, which encodes a polypeptide which is at least 95% identical to SEQ ID NO: 4.

12. The polynucleotide of claim 1, which encodes a polypeptide which is at least 97% identical to SEQ ID NO: 4.

13. The polynucleotide of claim 1, which encodes a polypeptide which is at least 99% identical to SEQ ID NO: 4.

14. The polynucleotide of claim 1, which encodes the polypeptide of SEQ ID NO: 4.

15. The isolated polynucleotide of claim 1, which encodes a polypeptide at least 95% identical to SEQ ID NO: 4 and that has at least one amino acid substitution between positions 38–48 of SEQ ID NO: 4, wherein expression of said polypeptide in a coryneform bacterium increases the production of lysine compared to expression of the polypeptide of SEQ ID NO: 2.

16. A vector comprising the isolated polynucleotide of claim 1.

17. A vector comprising the isolated polynucleotide of claim 6.

18. A vector comprising the isolated polynucleotide of claim 15.

19. A host cell comprising the isolated polynucleotide of claim 1.

20. The host cell of claim 19, wherein said polynucleotide is present in multiple copies.

21. The host cell of claim 19, further comprising a promoter, ribosome binding site, expression cassette or regulation region upstream from said polynucleotide.

22. The host cell of claim 19, which is a coryneform bacterium.

23. The host cell of claim 19, which is *Corynebacterium glutamicum*.

24. A host cell comprising the isolated polynucleotide of claim 6.

25. The host cell of claim 24, wherein said polynucleotide is present in multiple copies.

26. The host cell of claim 24, further comprising a promoter, ribosome binding site, expression cassette or regulation region upstream from said polynucleotide.

27. The host cell of claim 24, which is a coryneform bacterium.

28. The host cell of claim 24, which is *Corynebacterium glutamicum*.

29. A host cell comprising the isolated polynucleotide of claim 15.

30. The host cell of claim 29, wherein said polynucleotide is present in multiple copies.

31. The host cell of claim 29, further comprising a promoter, ribosome binding site, expression cassette or regulation region upstream from said polynucleotide.

32. The host cell of claim 29, which is a coryneform bacterium.

33. The host cell of claim 29, which is *Corynebacterium glutamicum*.

34. An isolated coryneform bacterium comprising the polynucleotide of claim 10.

35. *Corynebacterium glutamicum* strain DM1545 deposited as DSM 13992 at the Deutsche Sammlung für Mikroorganismen und Zellkulturen (DSMZ, German Collection of Microorganisms and Cell Cultures, Braunschweig, Germany).

36. A process for preparing an amino acid comprising;
    culturing the host cell of claim 19 in a medium for a time and under conditions suitable for the fermentive production of said amino acid, and
    recovering or isolating said amino acid.

37. The process of claim 36, wherein said amino acid is L-lysine.

38. A process for preparing an amino acid comprising:
    culturing the host cell of claim 24 in a medium for a time and under conditions suitable for the fermentive production of said amino acid, and
    recovering or isolating said amino acid.

39. The process of claim 38, wherein said amino acid is L-lysine.

40. A process for preparing an amino acid comprising:
    culturing the host cell of claim 29 in a medium for a time and under conditions suitable for the fermentive production of said amino acid, and
    recovering or isolating said amino acid.

41. The process of claim 40, wherein said amino acid is L-lysine.

42. The process of claim 36, wherein said host cell contains and over-expresses one or more of the genes selected from the group consisting of;
    the dapA gene which codes for dihydrodipicolinate synthase,
    the gap gene which codes for glyceraldehyde 3-phosphate dehydrogenase,
    the tpi gene which codes for triose phosphate isomerase,
    the pgk gene which codes for 3-phosphoglycerate kinase,
    the zwf gene which codes for glucose 6-phosphate dehydrogenase,
    the pyc gene which codes for pyruvate carboxylase,
    the mqo gene which codes for malate-quinone oxidoreductase,
    the lysC gene which codes for a feed-back resistant aspartate kinase,
    the lysE gene which codes for the lysine export protein,
    the zwa1 gene which codes for the Zwa1 protein, and
    the rpoB gene which codes for RNA polymerase B.

43. The process of claim 36, said host cell has been modified to reduce or eliminate the expression of one or more of the genes selected from the group consisting of:
    the pck gene which codes for phosphoenol pyruvate carboxykinase,
    the pgi gene which codes for glucose 6-phosphate isomerase,
    the poxB gene which codes for pyruvate oxidase,
    the zwa2 gene which codes for the Zwa2 protein.

* * * * *

SEQUENCE LISTING

<160> NUMBER OF SEQ ID NOS: 14

<210> SEQ ID NO 1
<211> LENGTH: 1775
<212> TYPE: DNA
<213> ORGANISM: Corynebacterium glutamicum
<220> FEATURE:
<221> NAME/KEY: CDS
<222> LOCATION: (500)..(880)
<223> OTHER INFORMATION:

<400> SEQUENCE: 1

```
cagctctaca agagtgtcta agtggcgggc attccatgct ttggaggagc gatcttcaaa      60
ttcctccaaa gtgagttgac ctcgggaaac agctgcagaa agttcatcca cgacttggtt     120
tcggttaagg tcagtggcga gcttctttgc tggttcgttt ccttgaggaa cagtcatggg     180
aaccattcta acaagggatt tggtgttttc tgcggctagc tgataatgtg aacggctgag     240
tcccactctt gtagttggga attgacggca cctcgcactc aagcgcggta tcgcccctgg     300
ttttccggga cgcggtggcg catgtttgca tttgatgagg ttgtccgtga catgtttggt     360
cgggccccaa aaagagcccc ctttttttgcg tgtctggaca cttttttcaaa tccttcgcca     420 tcgacaagct cagccttcgt gttcgtcccc cgggcgtcac gtcagcagtt aaagaacaac     480
tccgaaataa ggatggttc atg cca act att cag cag ctg gtc cgt aag ggc      532
                     Met Pro Thr Ile Gln Gln Leu Val Arg Lys Gly
                      1               5                  10 cgc cac gat aag tcc gcc aag gtg gct acc gcg gca ctg aag ggt tcc       580
Arg His Asp Lys Ser Ala Lys Val Ala Thr Ala Ala Leu Lys Gly Ser
                15                  20                  25 cct cag cgt cgt ggc gta tgc acc cgt gtg tac acc acc acc cct aag       628
Pro Gln Arg Arg Gly Val Cys Thr Arg Val Tyr Thr Thr Thr Pro Lys
         30                  35                  40 aag cct aac tct gct ctt cgt aag gtc gct cgt gtg cgc ctt acc tcc       676
Lys Pro Asn Ser Ala Leu Arg Lys Val Ala Arg Val Arg Leu Thr Ser
 45                  50                  55 ggc atc gag gtt tcc gct tac atc cct ggt gag ggc cac aac ctg cag       724
Gly Ile Glu Val Ser Ala Tyr Ile Pro Gly Glu Gly His Asn Leu Gln
 60                  65                  70                  75 gag cac tcc atg gtg ctc gtt cgc ggt ggt cgt gtt aag gac ctc cca       772
Glu His Ser Met Val Leu Val Arg Gly Gly Arg Val Lys Asp Leu Pro
                 80                  85                  90 ggt gtc cgt tac aag atc gtc cgt ggc gca ctg gat acc cag ggt gtt       820
Gly Val Arg Tyr Lys Ile Val Arg Gly Ala Leu Asp Thr Gln Gly Val
             95                 100                 105 aag gac cgc aag cag gct cgt tcc ccg cta cgg cgc gaa gag ggg ata       868
Lys Asp Arg Lys Gln Ala Arg Ser Pro Leu Arg Arg Glu Glu Gly Ile
        110                 115                 120 att aaa aat gcg taaatcagca gctcctaagc gtccagtagt tcaggaccct            920
Ile Lys Asn Ala
    125 gtatacaagt ccgagctcgt tacccagctc gtaaacaaga tcctcatcgg tgcaagaag       980 tccaccgcag agcgcatcgt ctacggtgca ctcgagatct gccgtgagaa gaccggcacc    1040 gatccagtag gaaccctcga gaaggctctc ggcaacgtgc gtccagacct cgaagttcgt    1100 tcccgccgtg ttggtggcgc tacctaccag gtgccagtgg atgttcgccc agagcgcgca    1160 aacaccctcg cactgcgttg gttggtaacc ttcacccgtc agcgtcgtga aacaccatg      1220 atcgagcgtc ttgcaaacga acttctggat gcagccaacg gccttggcgc ttccgtgaag    1280
```

```
cgtcgcgaag acacccacaa gatggcagag gccaaccgcg ccttcgctca ctaccgctgg    1340
tagtactgcc aagacatgaa agcccaatca cctttaagat caacgcctgc cggcgcccett   1400 cacatttgaa taagctggca gcctgcgttt cttcaaggcg actgggcttt tagtctcatt    1460
aatgcagttc accgctgtaa gatagctaaa tagaaacact gtttcggcag tgtgttacta   1520
aaaaatccat gtcacttgcc tcgagcgtgc tgcttgaatc gcaagttagt ggcaaaatgt    1580
aacaagagaa ttatccgtag gtgacaaact ttttaatact tgggtatctg tcatggatac    1640
cccggtaata aataagtgaa ttaccgtaac caacaagttg gggtaccact gtggcacaag    1700
aagtgcttaa ggatctaaac aaggtccgca acatcggcat catggcgcac atcgatgctg    1760
gtaagaccac gacca                                                    1775
```

<210> SEQ ID NO 2
<211> LENGTH: 127
<212> TYPE: PRT
<213> ORGANISM: Corynebacterium glutamicum

<400> SEQUENCE: 2

```
Met Pro Thr Ile Gln Gln Leu Val Arg Lys Gly Arg His Asp Lys Ser
1               5                   10                  15

Ala Lys Val Ala Thr Ala Ala Leu Lys Gly Ser Pro Gln Arg Arg Gly
            20                  25                  30

Val Cys Thr Arg Val Tyr Thr Thr Pro Lys Lys Pro Asn Ser Ala
        35                  40                  45

Leu Arg Lys Val Ala Arg Val Arg Leu Thr Ser Gly Ile Glu Val Ser
    50                  55                  60

Ala Tyr Ile Pro Gly Glu Gly His Asn Leu Gln Glu His Ser Met Val
65                  70                  75                  80

Leu Val Arg Gly Gly Arg Val Lys Asp Leu Pro Gly Val Arg Tyr Lys
                85                  90                  95

Ile Val Arg Gly Ala Leu Asp Thr Gln Gly Val Lys Asp Arg Lys Gln
            100                 105                 110

Ala Arg Ser Pro Leu Arg Arg Glu Glu Gly Ile Ile Lys Asn Ala
        115                 120                 125
```

<210> SEQ ID NO 3
<211> LENGTH: 1775
<212> TYPE: DNA
<213> ORGANISM: Corynebacterium glutamicum
<220> FEATURE:
<221> NAME/KEY: CDS
<222> LOCATION: (500)..(880)
<223> OTHER INFORMATION:

<400> SEQUENCE: 3

```
cagctctaca agagtgtcta agtggcgggc attccatgct ttggaggagc gatcttcaaa      60
ttcctccaaa gtgagttgac ctcgggaaac agctgcagaa agttcatcca cgacttggtt    120
tcggttaagg tcagtggcga gcttctttgc tggttcgttt ccttgaggaa cagtcatggg    180
aaccattcta acaagggatt tggtgttttc tgcggctagc tgataatgtg aacggctgag    240
tcccactctt gtagttggga attgacggca cctcgcactc aagcgcggta tcgcccctgg    300
ttttccggga cgcggtggcg catgtttgca tttgatgagg ttgtccgtga catgtttggt    360
cgggccccaa aaagagcccc ctttttttgcg tgtctggaca cttttttcaaa tccttcgcca    420 tcgacaagct cagccttcgt gttcgtcccc cgggcgtcac gtcagcagtt aaagaacaac    480
```

-continued

```
tccgaaataa ggatggttc atg cca act att cag cag ctg gtc cgt aag ggc        532
               Met Pro Thr Ile Gln Gln Leu Val Arg Lys Gly
                 1               5                  10 cgc cac gat aag tcc gcc aag gtg gct acc gcg gca ctg aag ggt tcc        580
Arg His Asp Lys Ser Ala Lys Val Ala Thr Ala Ala Leu Lys Gly Ser
            15                  20                  25 cct cag cgt cgt ggc gta tgc acc cgt gtg tac acc acc cct agg            628
Pro Gln Arg Arg Gly Val Cys Thr Arg Val Tyr Thr Thr Pro Arg
        30                  35                  40 aag cct aac tct gct ctt cgt aag gtc gct cgt gtg cgc ctt acc tcc        676
Lys Pro Asn Ser Ala Leu Arg Lys Val Ala Arg Val Arg Leu Thr Ser
    45                  50                  55 ggc atc gag gtt tcc gct tac atc cct ggt gag ggc cac aac ctg cag        724
Gly Ile Glu Val Ser Ala Tyr Ile Pro Gly Glu Gly His Asn Leu Gln
60                  65                  70                  75 gag cac tcc atg gtg ctc gtt cgc ggt ggt cgt gtt aag gac ctc cca        772
Glu His Ser Met Val Leu Val Arg Gly Gly Arg Val Lys Asp Leu Pro
                80                  85                  90 ggt gtc cgt tac aag atc gtc cgt ggc gca ctg gat acc cag ggt gtt        820
Gly Val Arg Tyr Lys Ile Val Arg Gly Ala Leu Asp Thr Gln Gly Val
            95                  100                 105 aag gac cgc aag cag gct cgt tcc ccg cta cgg cgc gaa gag ggg ata        868
Lys Asp Arg Lys Gln Ala Arg Ser Pro Leu Arg Arg Glu Glu Gly Ile
        110                 115                 120 att aaa aat gcg taaatcagca gctcctaagc gtccagtagt tcaggaccct            920
Ile Lys Asn Ala
    125 gtatacaagt ccgagctcgt tacccagctc gtaaacaaga tcctcatcgg tggcaagaag       980 tccaccgcag agcgcatcgt ctacggtgca ctcgagatct gccgtgagaa gaccggcacc      1040 gatccagtag gaaccctcga gaaggctctc ggcaacgtgc gtccagacct cgaagttcgt      1100 tcccgccgtg ttggtggcgc tacctaccag gtgccagtgg atgttcgccc agagcgcgca      1160 aacaccctcg cactgcgttg gttggtaacc ttcacccgtc agcgtcgtga aacaccatg       1220 atcgagcgtc ttgcaaacga acttctggat gcagccaacg gccttggcgc ttccgtgaag      1280 cgtcgcgaag acacccacaa gatggcagag gccaaccgcg ccttcgctca ctaccgctgg      1340 tagtactgcc aagacatgaa agcccaatca cctttaagat caacgcctgc cggcgccctt      1400 cacatttgaa taagctggca gcctgcgttt cttcaaggcg actgggcttt tagtctcatt      1460 aatgcagttc accgctgtaa gatagctaaa tagaaacact gtttcggcag tgtgttacta      1520 aaaaatccat gtcacttgcc tcgagcgtgc tgcttgaatc gcaagttagt ggcaaaatgt      1580 aacaagagaa ttatccgtag gtgacaaact ttttaatact tgggtatctg tcatggatac      1640 cccggtaata aataagtgaa ttaccgtaac caacaagttg gggtaccact gtggcacaag      1700 aagtgcttaa ggatctaaac aaggtccgca acatcggcat catggcgcac atcgatgctg      1760 gtaagaccac gacca                                                      1775
```

<210> SEQ ID NO 4
<211> LENGTH: 127
<212> TYPE: PRT
<213> ORGANISM: Corynebacterium glutamicum

<400> SEQUENCE: 4

Met Pro Thr Ile Gln Gln Leu Val Arg Lys Gly Arg His Asp Lys Ser
1               5                   10                  15

Ala Lys Val Ala Thr Ala Ala Leu Lys Gly Ser Pro Gln Arg Arg Gly
            20                  25                  30

```
Val Cys Thr Arg Val Tyr Thr Thr Pro Arg Lys Pro Asn Ser Ala
         35                  40                  45

Leu Arg Lys Val Ala Arg Val Arg Leu Thr Ser Gly Ile Glu Val Ser
     50                  55                  60

Ala Tyr Ile Pro Gly Glu Gly His Asn Leu Gln Glu His Ser Met Val
65                  70                  75                  80

Leu Val Arg Gly Gly Arg Val Lys Asp Leu Pro Gly Val Arg Tyr Lys
                 85                  90                  95

Ile Val Arg Gly Ala Leu Asp Thr Gln Gly Val Lys Asp Arg Lys Gln
            100                 105                 110

Ala Arg Ser Pro Leu Arg Arg Glu Glu Gly Ile Ile Lys Asn Ala
        115                 120                 125

<210> SEQ ID NO 5
<211> LENGTH: 5099
<212> TYPE: DNA
<213> ORGANISM: Corynebacterium glutamicum
<220> FEATURE:
<221> NAME/KEY: CDS
<222> LOCATION: (702)..(4196)
<223> OTHER INFORMATION:

<400> SEQUENCE: 5
```

| | | | |
|---|---|---|---|
| acaatgtgac tcgtgatttt tgggtggatc agcgtaccgg tttggttgtc gatctagctg | | | 60 |
| aaaatattga tgatttttac ggcgaccgca gcggccagaa gtacgaacag aaattgcttt | | | 120 |
| tcgacgcctc cctcgacgat gcagctgtct ctaagctggt tgcacaggcc gaaagcatcc | | | 180 |
| ctgatggaga tgtgagcaaa atcgcaaata ccgtaggtat tgtgatcggt gcggtattgg | | | 240 |
| ctctcgtggg cctggccggg tgttttgggg cgtttgggaa gaaacgtcga gaagcttaac | | | 300 |
| ctgctgttca atagattttt ccctgtttcg aattgcggaa accccgggtt tgtttgctag | | | 360 |
| ggtgcctcgt agaagggggtc aagaagattt ctgggaaacg cgcccgtgcg gttggttgct | | | 420 |
| aatagcacgc ggagcaccag atgaaaaatc tcccctttac tttcgcgcgc gattggtata | | | 480 |
| ctctgagtcg ttgcgttgga attcgtgact cttttttcgtt cctgtagcgc caagaccttg | | | 540 |
| atcaaggtgg tttaaaaaaa ccgatttgac aaggtcattc agtgctatct ggagtcgttc | | | 600 |
| aggggggatcg ggttcctcag cagaccaatt gctcaaaaat accagcggtg ttgatctgca | | | 660 |
| cttaatggcc ttgaccagcc aggtgcaatt acccgcgtga g gtg ctg gaa gga ccc | | | 716 |
| | | Val Leu Glu Gly Pro | |
| | | 1 5 | |

```
atc ttg gca gtc tcc cgc cag acc aag tca gtc gtc gat att ccc ggt      764
Ile Leu Ala Val Ser Arg Gln Thr Lys Ser Val Val Asp Ile Pro Gly
             10                  15                  20 gca ccg cag cgt tat tct ttc gcg aag gtg tcc gca ccc att gag gtg      812
Ala Pro Gln Arg Tyr Ser Phe Ala Lys Val Ser Ala Pro Ile Glu Val
         25                  30                  35 ccc ggg cta cta gat ctt caa ctg gat tct tac tcc tgg ctg att ggt      860
Pro Gly Leu Leu Asp Leu Gln Leu Asp Ser Tyr Ser Trp Leu Ile Gly
         40                  45                  50 acg cct gag tgg cgt gct cgt cag aag gaa gaa ttc ggc gag gga gcc      908
Thr Pro Glu Trp Arg Ala Arg Gln Lys Glu Glu Phe Gly Glu Gly Ala
 55                  60                  65 cgc gta acc agc ggc ctt gag aac att ctc gag gag ctc tcc cca atc      956
Arg Val Thr Ser Gly Leu Glu Asn Ile Leu Glu Glu Leu Ser Pro Ile
 70                  75                  80                  85 cag gat tac tct gga aac atg tcc ctg agc ctt tcg gag cca cgc ttc     1004
Gln Asp Tyr Ser Gly Asn Met Ser Leu Ser Leu Ser Glu Pro Arg Phe
             90                  95                 100
```

-continued

```
gaa gac gtc aag aac acc att gac gag gcg aaa gaa aag gac atc aac    1052
Glu Asp Val Lys Asn Thr Ile Asp Glu Ala Lys Glu Lys Asp Ile Asn
            105                 110                 115 tac gcg gcg cca ctg tat gtg acc gcg gag ttc gtc aac aac acc acc    1100
Tyr Ala Ala Pro Leu Tyr Val Thr Ala Glu Phe Val Asn Asn Thr Thr
        120                 125                 130 ggt gaa atc aag tct cag act gtc ttc atc ggc gat ttc cca atg atg    1148
Gly Glu Ile Lys Ser Gln Thr Val Phe Ile Gly Asp Phe Pro Met Met
    135                 140                 145 acg gac aag gga acg ttc atc atc aac gga acc gaa cgc gtt gtg gtc    1196
Thr Asp Lys Gly Thr Phe Ile Ile Asn Gly Thr Glu Arg Val Val Val
150                 155                 160                 165 agc cag ctc gtc cgc tcc ccg ggc gtg tac ttt gac cag acc atc gat    1244
Ser Gln Leu Val Arg Ser Pro Gly Val Tyr Phe Asp Gln Thr Ile Asp
                170                 175                 180 aag tca act gag cgt cca ctg cac gcc gtg aag gtt att cct tcc cgt    1292
Lys Ser Thr Glu Arg Pro Leu His Ala Val Lys Val Ile Pro Ser Arg
            185                 190                 195 ggt gct tgg ctt gag ttt gac gtc gat aag cgc gat tcg gtt ggt gtt    1340
Gly Ala Trp Leu Glu Phe Asp Val Asp Lys Arg Asp Ser Val Gly Val
        200                 205                 210 cgt att gac cgc aag cgt cgc cag cca gtc acc gta ctg ctg aag gct    1388
Arg Ile Asp Arg Lys Arg Arg Gln Pro Val Thr Val Leu Leu Lys Ala
    215                 220                 225 ctt ggc tgg acc act gag cag atc acc gag cgt ttc ggt ttc tct gaa    1436
Leu Gly Trp Thr Thr Glu Gln Ile Thr Glu Arg Phe Gly Phe Ser Glu
230                 235                 240                 245 atc atg atg tcc acc ctc gag tcc gat ggt gta gca aac acc gat gag    1484
Ile Met Met Ser Thr Leu Glu Ser Asp Gly Val Ala Asn Thr Asp Glu
                250                 255                 260 gca ttg ctg gag atc tac cgc aag cag cgt cca ggc gag cag cct acc    1532
Ala Leu Leu Glu Ile Tyr Arg Lys Gln Arg Pro Gly Glu Gln Pro Thr
            265                 270                 275 cgc gac ctt gcg cag tcc ctc ctg gac aac agc ttc ttc cgt gca aag    1580
Arg Asp Leu Ala Gln Ser Leu Leu Asp Asn Ser Phe Phe Arg Ala Lys
        280                 285                 290 cgc tac gac ctg gct cgc gtt ggt cgt tac aag atc aac cgc aag ctc    1628
Arg Tyr Asp Leu Ala Arg Val Gly Arg Tyr Lys Ile Asn Arg Lys Leu
    295                 300                 305 ggc ctt ggt ggc gac cac gat ggt ttg atg act ctt act gaa gag gac    1676
Gly Leu Gly Gly Asp His Asp Gly Leu Met Thr Leu Thr Glu Glu Asp
310                 315                 320                 325 atc gca acc acc atc gag tac ctg gtg cgt ctg cac gca ggt gag cgc    1724
Ile Ala Thr Thr Ile Glu Tyr Leu Val Arg Leu His Ala Gly Glu Arg
                330                 335                 340 gtc atg act tct cca aat ggt gaa gag atc cca gtc gag acc gat gac    1772
Val Met Thr Ser Pro Asn Gly Glu Glu Ile Pro Val Glu Thr Asp Asp
            345                 350                 355 atc gac cac ttt ggt aac cgt cgt ctg cgt acc gtt ggc gaa ctg atc    1820
Ile Asp His Phe Gly Asn Arg Arg Leu Arg Thr Val Gly Glu Leu Ile
        360                 365                 370 cag aac cag gtc cgt gtc ggc ctg tcc cgc atg gag cgc gtt gtt cgt    1868
Gln Asn Gln Val Arg Val Gly Leu Ser Arg Met Glu Arg Val Val Arg
    375                 380                 385 gag cgt atg acc acc cag gat gcg gag tcc att act cct act tcc ttg    1916
Glu Arg Met Thr Thr Gln Asp Ala Glu Ser Ile Thr Pro Thr Ser Leu
390                 395                 400                 405 atc aac gtt cgt cct gtc tct gca gct atc cgt gag ttc ttc gga act    1964
Ile Asn Val Arg Pro Val Ser Ala Ala Ile Arg Glu Phe Phe Gly Thr
                410                 415                 420
```

```
tcc cag ctg tct cag ttc atg gtc cag aac aac tcc ctg tct ggt ttg      2012
Ser Gln Leu Ser Gln Phe Met Val Gln Asn Asn Ser Leu Ser Gly Leu
            425                 430                 435 act cac aag cgt cgt ctg tcg gct ctg ggc ccg ggt ggt ctg tcc cgt      2060
Thr His Lys Arg Arg Leu Ser Ala Leu Gly Pro Gly Gly Leu Ser Arg
        440                 445                 450 gag cgc gcc ggc atc gag gtt cga gac gtt cac cca tct cac tac ggc      2108
Glu Arg Ala Gly Ile Glu Val Arg Asp Val His Pro Ser His Tyr Gly
    455                 460                 465 cgt atg tgc cca att gag act ccg gaa ggt cca aac att ggc ctg atc      2156
Arg Met Cys Pro Ile Glu Thr Pro Glu Gly Pro Asn Ile Gly Leu Ile
470                 475                 480                 485 ggt tcc ttg gct tcc tat gct cga gtg aac cca ttc ggt ttc att gag      2204
Gly Ser Leu Ala Ser Tyr Ala Arg Val Asn Pro Phe Gly Phe Ile Glu
                490                 495                 500 acc cca tac cgt cgc atc atc gac ggc aag ctg acc gac cag att gac      2252
Thr Pro Tyr Arg Arg Ile Ile Asp Gly Lys Leu Thr Asp Gln Ile Asp
            505                 510                 515 tac ctt acc gct gat gag gaa gac cgc ttc gtt gtt gcg cag gca aac      2300
Tyr Leu Thr Ala Asp Glu Glu Asp Arg Phe Val Val Ala Gln Ala Asn
        520                 525                 530 acg cac tac gac gaa gag ggc aac atc acc gat gag acc gtc act gtt      2348
Thr His Tyr Asp Glu Glu Gly Asn Ile Thr Asp Glu Thr Val Thr Val
    535                 540                 545 cgt ctg aag gac ggc gac atc gcc atg gtt ggc cgc aac gcg gtt gat      2396
Arg Leu Lys Asp Gly Asp Ile Ala Met Val Gly Arg Asn Ala Val Asp
550                 555                 560                 565 tac atg gac gtt tcc cct cgt cag atg gtt tct gtt ggt acc gcg atg      2444
Tyr Met Asp Val Ser Pro Arg Gln Met Val Ser Val Gly Thr Ala Met
                570                 575                 580 att cca ttc ctg gag cac gac gat gct aac cgt gca ctg atg ggc gcg      2492
Ile Pro Phe Leu Glu His Asp Asp Ala Asn Arg Ala Leu Met Gly Ala
            585                 590                 595 aac atg cag aag cag gct gtg cca ctg att cgt gcc gag gct cct ttc      2540
Asn Met Gln Lys Gln Ala Val Pro Leu Ile Arg Ala Glu Ala Pro Phe
        600                 605                 610 gtg ggc acc ggt atg gag cag cgc gca gca tac gac gcc ggc gac ctg      2588
Val Gly Thr Gly Met Glu Gln Arg Ala Ala Tyr Asp Ala Gly Asp Leu
    615                 620                 625 gtt att acc cca gtc gca ggt gtg gtg gaa aac gtt tca gct gac ttc      2636
Val Ile Thr Pro Val Ala Gly Val Val Glu Asn Val Ser Ala Asp Phe
630                 635                 640                 645 atc acc atc atg gct gat gac ggc aag cgc gaa acc tac ctg ctg cgt      2684
Ile Thr Ile Met Ala Asp Asp Gly Lys Arg Glu Thr Tyr Leu Leu Arg
                650                 655                 660 aag ttc cag cgc acc aac cag ggc acc agc tac aac cag aag cct ttg      2732
Lys Phe Gln Arg Thr Asn Gln Gly Thr Ser Tyr Asn Gln Lys Pro Leu
            665                 670                 675 gtt aac ttg ggc gag cgc gtt gaa gct ggc cag gtt att gct gat ggt      2780
Val Asn Leu Gly Glu Arg Val Glu Ala Gly Gln Val Ile Ala Asp Gly
        680                 685                 690 cca ggt acc ttc aat ggt gaa atg tcc ctt ggc cgt aac ctt ctg gtt      2828
Pro Gly Thr Phe Asn Gly Glu Met Ser Leu Gly Arg Asn Leu Leu Val
    695                 700                 705 gcg ttc atg cct tgg gaa ggc cac aac tac gag gat gcg atc atc ctc      2876
Ala Phe Met Pro Trp Glu Gly His Asn Tyr Glu Asp Ala Ile Ile Leu
710                 715                 720                 725 aac cag aac atc gtt gag cag gac atc ttg acc tcg atc cac atc gag      2924
Asn Gln Asn Ile Val Glu Gln Asp Ile Leu Thr Ser Ile His Ile Glu
                730                 735                 740
```

```
gag cac gag atc gat gcc cgc gac act aag ctt ggc gcc gaa gaa atc      2972
Glu His Glu Ile Asp Ala Arg Asp Thr Lys Leu Gly Ala Glu Glu Ile
            745                 750                 755 acc cgc gac atc cct aat gtg tct gaa gaa gtc ctc aag gac ctc gac      3020
Thr Arg Asp Ile Pro Asn Val Ser Glu Glu Val Leu Lys Asp Leu Asp
        760                 765                 770 gac cgc ggt att gtc cgc atc ggt gct gat gtt cgt gac ggc gac atc      3068
Asp Arg Gly Ile Val Arg Ile Gly Ala Asp Val Arg Asp Gly Asp Ile
    775                 780                 785 ctg gtc ggt aag gtc acc cct aag ggc gag acc gag ctc acc ccg gaa      3116
Leu Val Gly Lys Val Thr Pro Lys Gly Glu Thr Glu Leu Thr Pro Glu
790                 795                 800                 805 gag cgc ttg ctg cgc gca atc ttc ggt gag aag gcc cgc gaa gtt cgc      3164
Glu Arg Leu Leu Arg Ala Ile Phe Gly Glu Lys Ala Arg Glu Val Arg
                810                 815                 820 gat acc tcc atg aag gtg cct cac ggt gag acc ggc aag gtc atc ggc      3212
Asp Thr Ser Met Lys Val Pro His Gly Glu Thr Gly Lys Val Ile Gly
            825                 830                 835 gtg cgt cac ttc tcc cgc gag gac gac gac gat ctg gct cct ggc gtc      3260
Val Arg His Phe Ser Arg Glu Asp Asp Asp Asp Leu Ala Pro Gly Val
        840                 845                 850 aac gag atg atc cgt atc tac gtt gct cag aag cgt aag atc cag gac      3308
Asn Glu Met Ile Arg Ile Tyr Val Ala Gln Lys Arg Lys Ile Gln Asp
    855                 860                 865 ggc gat aag ctc gct ggc cgc cac ggt aac aag ggt gtt gtc ggt aaa      3356
Gly Asp Lys Leu Ala Gly Arg His Gly Asn Lys Gly Val Val Gly Lys
870                 875                 880                 885 att ttg cct cag gaa gat atg cca ttc ctt cca gac ggc act cct gtt      3404
Ile Leu Pro Gln Glu Asp Met Pro Phe Leu Pro Asp Gly Thr Pro Val
                890                 895                 900 gac atc atc ttg aac acc cac ggt gtt cca cgt cgt atg aac att ggt      3452
Asp Ile Ile Leu Asn Thr His Gly Val Pro Arg Arg Met Asn Ile Gly
            905                 910                 915 cag gtt ctt gag acc cac ctt ggc tgg ctg gca tct gct ggt tgg tcc      3500
Gln Val Leu Glu Thr His Leu Gly Trp Leu Ala Ser Ala Gly Trp Ser
        920                 925                 930 gtg gat cct gaa gat cct gag aac gct gag ctc gtc aag act ctg cct      3548
Val Asp Pro Glu Asp Pro Glu Asn Ala Glu Leu Val Lys Thr Leu Pro
    935                 940                 945 gca gac ctc ctc gag gtt cct gct ggt tcc ttg act gca act cct gtg      3596
Ala Asp Leu Leu Glu Val Pro Ala Gly Ser Leu Thr Ala Thr Pro Val
950                 955                 960                 965 ttc gac ggt gcg tca aac gaa gag ctc gca ggc ctg ctc gct aat tca      3644
Phe Asp Gly Ala Ser Asn Glu Glu Leu Ala Gly Leu Leu Ala Asn Ser
                970                 975                 980 cgt cca aac cgc gac ggc gac gtc atg gtt aac gcg gat ggt aaa gca      3692
Arg Pro Asn Arg Asp Gly Asp Val Met Val Asn Ala Asp Gly Lys Ala
            985                 990                 995 acg ctt atc gac ggt cgc tcc ggt gag cct tac ccg tac ccg gtt         3737
Thr Leu Ile Asp Gly Arg Ser Gly Glu Pro Tyr Pro Tyr Pro Val
        1000                1005                1010 tcc atc ggc tac atg tac atg ctg aag ctg cac cac ctc gtt gac         3782
Ser Ile Gly Tyr Met Tyr Met Leu Lys Leu His His Leu Val Asp
    1015                1020                1025 gag aag atc cac gca cgt tcc act ggt cct tac tcc atg att acc         3827
Glu Lys Ile His Ala Arg Ser Thr Gly Pro Tyr Ser Met Ile Thr
1030                1035                1040 cag cag cca ctg ggt ggt aaa gca cag ttc ggt gga cag cgt ttc         3872
Gln Gln Pro Leu Gly Gly Lys Ala Gln Phe Gly Gly Gln Arg Phe
                1045                1050                1055
```

|   |   |   |   |   |   |   |   |   |   |   |   |   |   |   | |
|---|---|---|---|---|---|---|---|---|---|---|---|---|---|---|---|
| ggc | gaa | atg | gag | gtg | tgg | gca | atg | cag | gca | tac | ggc | gct | gcc | tac | 3917 |
| Gly | Glu | Met | Glu | Val | Trp | Ala | Met | Gln | Ala | Tyr | Gly | Ala | Ala | Tyr | |
|   |   | 1060 |   |   |   |   | 1065 |   |   |   | 1070 |   |   |   | |
| aca | ctt | cag | gag | ctg | ctg | acc | atc | aag | tct | gat | gac | gtg | gtt | ggc | 3962 |
| Thr | Leu | Gln | Glu | Leu | Leu | Thr | Ile | Lys | Ser | Asp | Asp | Val | Val | Gly | |
|   | 1075 |   |   |   |   | 1080 |   |   |   |   | 1085 |   |   |   | |
| cgt | gtc | aag | gtc | tac | gaa | gca | att | gtg | aag | ggc | gag | aac | atc | ccg | 4007 |
| Arg | Val | Lys | Val | Tyr | Glu | Ala | Ile | Val | Lys | Gly | Glu | Asn | Ile | Pro | |
|   | 1090 |   |   |   |   | 1095 |   |   |   |   | 1100 |   |   |   | |
| gat | cca | ggt | att | cct | gag | tcc | ttc | aag | gtt | ctc | ctc | aag | gag | ctc | 4052 |
| Asp | Pro | Gly | Ile | Pro | Glu | Ser | Phe | Lys | Val | Leu | Leu | Lys | Glu | Leu | |
|   | 1105 |   |   |   |   | 1110 |   |   |   |   | 1115 |   |   |   | |
| cag | tcc | ttg | tgc | ctg | aac | gtg | gag | gtt | ctc | tcc | gca | gac | ggc | act | 4097 |
| Gln | Ser | Leu | Cys | Leu | Asn | Val | Glu | Val | Leu | Ser | Ala | Asp | Gly | Thr | |
|   | 1120 |   |   |   |   | 1125 |   |   |   |   | 1130 |   |   |   | |
| cca | atg | gag | ctc | gcg | ggt | gac | gac | gac | gac | ttc | gat | cag | gca | ggc | 4142 |
| Pro | Met | Glu | Leu | Ala | Gly | Asp | Asp | Asp | Asp | Phe | Asp | Gln | Ala | Gly | |
|   | 1135 |   |   |   |   | 1140 |   |   |   |   | 1145 |   |   |   | |
| gcc | tca | ctt | ggc | atc | aac | ctg | tcc | cgt | gac | gag | cgt | tcc | gac | gcc | 4187 |
| Ala | Ser | Leu | Gly | Ile | Asn | Leu | Ser | Arg | Asp | Glu | Arg | Ser | Asp | Ala | |
|   | 1150 |   |   |   |   | 1155 |   |   |   |   | 1160 |   |   |   | |
| gac | acc | gca | tagcagatca gaaaacaacc gctagaaatc aagccataca |   |   |   |   |   |   |   |   |   |   |   | 4236 |
| Asp | Thr | Ala | | | | | | | | | | | | | |
|   | 1165 |   | | | | | | | | | | | | | |

```
tcccccggac attgaagaga tgttctgggg ggaaagggag ttttacgtgc tcgacgtaaa    4296
cgtcttcgat gagctccgca tcggcctggc caccgccgac gacatccgcc gttggtccaa    4356
gggtgaggtc aagaagccgg agaccatcaa ctaccgaacc ctcaagcctg agaaggacgg    4416
tctgttctgc gagcgtatct tcggtccaac tcgcgactgg gagtgcgcct gcggtaagta    4476
caagcgtgtc cgctacaagg gcatcatctg tgaacgctgt ggcgttgagg tcaccaagtc    4536
caaggtgcgc cgtgagcgca tgggacacat tgagctcgct gcaccagtaa cccacatttg    4596
gtacttcaag ggcgttccat cacgcctcgg ctacctttg gaccttgctc caaaggaccct    4656
ggacctcatc atctacttcg gtgcgaacat catcaccagc gtggacgaag aggctcgcca    4716
cagcgaccag accactcttg aggcagaaat gcttctggag aagaaggacg ttgaggcaga    4776
cgcagagtct gacattgctg agcgtgctga aaagctcgaa gaggatcttg ctgaacttga    4836
ggcagctggc gctaaggccg acgctcgccc caaggttcag gctgctgccg ataaggaaat    4896
gcagcacatc cgtgagcgtg cacagcgcga atcgatcgt ctcgatgagg tctggcagac    4956
cttcatcaag cttgctccaa agcagatgat ccgcgatgag aagctctacg atgaactgat    5016
cgaccgctac gaggattact tcaccggtgg tatgggtgca gagtccattg aggctttgat    5076
ccagaacttc gaccttgatg ctg                                            5099
```

<210> SEQ ID NO 6
<211> LENGTH: 1165
<212> TYPE: PRT
<213> ORGANISM: Corynebacterium glutamicum

<400> SEQUENCE: 6

```
Val Leu Glu Gly Pro Ile Leu Ala Val Ser Arg Gln Thr Lys Ser Val
  1               5                  10                  15

Val Asp Ile Pro Gly Ala Pro Gln Arg Tyr Ser Phe Ala Lys Val Ser
             20                  25                  30

Ala Pro Ile Glu Val Pro Gly Leu Leu Asp Leu Gln Leu Asp Ser Tyr
         35                  40                  45
```

-continued

```
Ser Trp Leu Ile Gly Thr Pro Glu Trp Arg Ala Arg Gln Lys Glu Glu
 50                  55                  60
Phe Gly Glu Gly Ala Arg Val Thr Ser Gly Leu Glu Asn Ile Leu Glu
 65                  70                  75                  80
Glu Leu Ser Pro Ile Gln Asp Tyr Ser Gly Asn Met Ser Leu Ser Leu
                 85                  90                  95
Ser Glu Pro Arg Phe Glu Asp Val Lys Asn Thr Ile Asp Glu Ala Lys
             100                 105                 110
Glu Lys Asp Ile Asn Tyr Ala Ala Pro Leu Tyr Val Thr Ala Glu Phe
         115                 120                 125
Val Asn Asn Thr Thr Gly Glu Ile Lys Ser Gln Thr Val Phe Ile Gly
130                 135                 140
Asp Phe Pro Met Met Thr Asp Lys Gly Thr Phe Ile Ile Asn Gly Thr
145                 150                 155                 160
Glu Arg Val Val Val Ser Gln Leu Val Arg Ser Pro Gly Val Tyr Phe
                165                 170                 175
Asp Gln Thr Ile Asp Lys Ser Thr Glu Arg Pro Leu His Ala Val Lys
            180                 185                 190
Val Ile Pro Ser Arg Gly Ala Trp Leu Glu Phe Asp Val Asp Lys Arg
        195                 200                 205
Asp Ser Val Gly Val Arg Ile Asp Arg Lys Arg Arg Gln Pro Val Thr
210                 215                 220
Val Leu Leu Lys Ala Leu Gly Trp Thr Thr Glu Gln Ile Thr Glu Arg
225                 230                 235                 240
Phe Gly Phe Ser Glu Ile Met Met Ser Thr Leu Glu Ser Asp Gly Val
                245                 250                 255
Ala Asn Thr Asp Glu Ala Leu Leu Glu Ile Tyr Arg Lys Gln Arg Pro
            260                 265                 270
Gly Glu Gln Pro Thr Arg Asp Leu Ala Gln Ser Leu Leu Asp Asn Ser
        275                 280                 285
Phe Phe Arg Ala Lys Arg Tyr Asp Leu Ala Arg Val Gly Arg Tyr Lys
290                 295                 300
Ile Asn Arg Lys Leu Gly Leu Gly Gly Asp His Asp Gly Leu Met Thr
305                 310                 315                 320
Leu Thr Glu Glu Asp Ile Ala Thr Thr Ile Glu Tyr Leu Val Arg Leu
                325                 330                 335
His Ala Gly Glu Arg Val Met Thr Ser Pro Asn Gly Glu Glu Ile Pro
            340                 345                 350
Val Glu Thr Asp Asp Ile Asp His Phe Gly Asn Arg Arg Leu Arg Thr
        355                 360                 365
Val Gly Glu Leu Ile Gln Asn Gln Val Arg Val Gly Leu Ser Arg Met
370                 375                 380
Glu Arg Val Val Arg Glu Arg Met Thr Thr Gln Asp Ala Glu Ser Ile
385                 390                 395                 400
Thr Pro Thr Ser Leu Ile Asn Val Arg Pro Val Ser Ala Ala Ile Arg
                405                 410                 415
Glu Phe Phe Gly Thr Ser Gln Leu Ser Gln Phe Met Val Gln Asn Asn
            420                 425                 430
Ser Leu Ser Gly Leu Thr His Lys Arg Arg Leu Ser Ala Leu Gly Pro
        435                 440                 445
Gly Gly Leu Ser Arg Glu Arg Ala Gly Ile Glu Val Arg Asp Val His
450                 455                 460
```

-continued

```
Pro Ser His Tyr Gly Arg Met Cys Pro Ile Glu Thr Pro Glu Gly Pro
465                 470                 475                 480

Asn Ile Gly Leu Ile Gly Ser Leu Ala Ser Tyr Ala Arg Val Asn Pro
            485                 490                 495

Phe Gly Phe Ile Glu Thr Pro Tyr Arg Arg Ile Ile Asp Gly Lys Leu
            500                 505                 510

Thr Asp Gln Ile Asp Tyr Leu Thr Ala Asp Glu Glu Asp Arg Phe Val
            515                 520                 525

Val Ala Gln Ala Asn Thr His Tyr Asp Glu Glu Gly Asn Ile Thr Asp
            530                 535                 540

Glu Thr Val Thr Val Arg Leu Lys Asp Gly Asp Ile Ala Met Val Gly
545                 550                 555                 560

Arg Asn Ala Val Asp Tyr Met Asp Val Ser Pro Arg Gln Met Val Ser
                565                 570                 575

Val Gly Thr Ala Met Ile Pro Phe Leu Glu His Asp Asp Ala Asn Arg
            580                 585                 590

Ala Leu Met Gly Ala Asn Met Gln Lys Gln Ala Val Pro Leu Ile Arg
            595                 600                 605

Ala Glu Ala Pro Phe Val Gly Thr Gly Met Glu Gln Arg Ala Ala Tyr
            610                 615                 620

Asp Ala Gly Asp Leu Val Ile Thr Pro Val Ala Gly Val Val Glu Asn
625                 630                 635                 640

Val Ser Ala Asp Phe Ile Thr Ile Met Ala Asp Asp Gly Lys Arg Glu
                645                 650                 655

Thr Tyr Leu Leu Arg Lys Phe Gln Arg Thr Asn Gln Gly Thr Ser Tyr
            660                 665                 670

Asn Gln Lys Pro Leu Val Asn Leu Gly Glu Arg Val Glu Ala Gly Gln
            675                 680                 685

Val Ile Ala Asp Gly Pro Gly Thr Phe Asn Gly Glu Met Ser Leu Gly
690                 695                 700

Arg Asn Leu Leu Val Ala Phe Met Pro Trp Glu Gly His Asn Tyr Glu
705                 710                 715                 720

Asp Ala Ile Ile Leu Asn Gln Asn Ile Val Glu Gln Asp Ile Leu Thr
            725                 730                 735

Ser Ile His Ile Glu Glu His Glu Ile Asp Ala Arg Asp Thr Lys Leu
            740                 745                 750

Gly Ala Glu Glu Ile Thr Arg Asp Ile Pro Asn Val Ser Glu Glu Val
            755                 760                 765

Leu Lys Asp Leu Asp Asp Arg Gly Ile Val Arg Ile Gly Ala Asp Val
770                 775                 780

Arg Asp Gly Asp Ile Leu Val Gly Lys Val Thr Pro Lys Gly Glu Thr
785                 790                 795                 800

Glu Leu Thr Pro Glu Glu Arg Leu Leu Arg Ala Ile Phe Gly Glu Lys
            805                 810                 815

Ala Arg Glu Val Arg Asp Thr Ser Met Lys Val Pro His Gly Glu Thr
            820                 825                 830

Gly Lys Val Ile Gly Val Arg His Phe Ser Arg Glu Asp Asp Asp
            835                 840                 845

Leu Ala Pro Gly Val Asn Glu Met Ile Arg Ile Tyr Val Ala Gln Lys
            850                 855                 860

Arg Lys Ile Gln Asp Gly Asp Lys Leu Ala Gly Arg His Gly Asn Lys
865                 870                 875                 880
```

-continued

Gly Val Val Gly Lys Ile Leu Pro Gln Glu Asp Met Pro Phe Leu Pro
            885                 890                 895

Asp Gly Thr Pro Val Asp Ile Ile Leu Asn Thr His Gly Val Pro Arg
        900                 905                 910

Arg Met Asn Ile Gly Gln Val Leu Glu Thr His Leu Gly Trp Leu Ala
            915                 920                 925

Ser Ala Gly Trp Ser Val Asp Pro Glu Asp Pro Glu Asn Ala Glu Leu
        930                 935                 940

Val Lys Thr Leu Pro Ala Asp Leu Leu Glu Val Pro Ala Gly Ser Leu
945                 950                 955                 960

Thr Ala Thr Pro Val Phe Asp Gly Ala Ser Asn Glu Glu Leu Ala Gly
                965                 970                 975

Leu Leu Ala Asn Ser Arg Pro Asn Arg Asp Gly Asp Val Met Val Asn
            980                 985                 990

Ala Asp Gly Lys Ala Thr Leu Ile Asp Gly Arg Ser Gly Glu Pro Tyr
        995                 1000                1005

Pro Tyr Pro Val Ser Ile Gly Tyr Met Tyr Met Leu Lys Leu His
    1010                1015                1020

His Leu Val Asp Glu Lys Ile His Ala Arg Ser Thr Gly Pro Tyr
    1025                1030                1035

Ser Met Ile Thr Gln Gln Pro Leu Gly Gly Lys Ala Gln Phe Gly
    1040                1045                1050

Gly Gln Arg Phe Gly Glu Met Glu Val Trp Ala Met Gln Ala Tyr
    1055                1060                1065

Gly Ala Ala Tyr Thr Leu Gln Glu Leu Leu Thr Ile Lys Ser Asp
    1070                1075                1080

Asp Val Val Gly Arg Val Lys Val Tyr Glu Ala Ile Val Lys Gly
    1085                1090                1095

Glu Asn Ile Pro Asp Pro Gly Ile Pro Glu Ser Phe Lys Val Leu
    1100                1105                1110

Leu Lys Glu Leu Gln Ser Leu Cys Leu Asn Val Glu Val Leu Ser
    1115                1120                1125

Ala Asp Gly Thr Pro Met Glu Leu Ala Gly Asp Asp Asp Phe
    1130                1135                1140

Asp Gln Ala Gly Ala Ser Leu Gly Ile Asn Leu Ser Arg Asp Glu
    1145                1150                1155

Arg Ser Asp Ala Asp Thr Ala
    1160                1165

<210> SEQ ID NO 7
<211> LENGTH: 151
<212> TYPE: DNA
<213> ORGANISM: Corynebacterium glutamicum

<400> SEQUENCE: 7
ggttgccggt aatcctgttg cggacaatat ttacaggatc tgacacattg gcatcgctg        60 ggggagtggt ctcgtaggcc gccggcgcat aggaggcgcc gggaaattgc tgaccaagca      120
gagtgtaggg attgtcgttc acatcagaga t                                     151

<210> SEQ ID NO 8
<211> LENGTH: 1926
<212> TYPE: DNA
<213> ORGANISM: Corynebacterium glutamicum

<400> SEQUENCE: 8

```
ggttgccggt aatcctgttg cggacaatat ttacaggatc tgacacattg ggcatcgctg        60
ggggagtggt ctcgtaggcc gccggcgcat aggaggcgcc gggaaattgc tgaccaagca       120
gagtgtaggg attgtcgttc acatcagaga tcagctctac aagagtgtct aagtggcggg       180
cattccatgc tttggaggag cgatcttcaa attcctccaa agtgagttga cctcgggaaa       240
cagctgcaga agttcatcc acgacttggt ttcggttaag gtcagtggcg agcttctttg        300
ctggttcgtt tccttgagga acagtcatgg gaaccattct aacaagggat ttggtgtttt       360
ctgcggctag ctgataatgt gaacggctga gtcccactct tgtagttggg aattgacggc       420
acctcgcact caagcgcggt atcgcccctg gttttcgggg acgcggtggc gcatgtttgc       480
atttgatgag gttgtccgtg acatgtttgg tcgggcccca aaaagagccc cctttttgc        540
gtgtctggac acttttcaa atccttcgcc atcgacaagc tcagccttcg tgttcgtccc        600
ccgggcgtca cgtcagcagt taaagaacaa ctccgaaata aggatggttc atgccaacta       660
ttcagcagct ggtccgtaag ggccgccacg ataagtccgc caaggtggct accgcggcac       720
tgaagggttc ccctcagcgt cgtggcgtat gcacccgtgt gtacaccacc accccctaaga      780
agcctaactc tgctcttcgt aaggtcgctc gtgtgcgcct tacctccggc atcgaggttt       840
ccgcttacat ccctggtgag ggccacaacc tgcaggagca ctccatggtg ctcgttcgcg       900
gtggtcgtgt taaggacctc ccaggtgtcc gttacaagat cgtccgtggc gcactggata       960
cccagggtgt taaggaccgc aagcaggctc gttccccgct acggcgcgaa gaggggataa      1020
ttaaaaatgc gtaaatcagc agctcctaag cgtccagtag ttcaggaccc tgtatacaag      1080
tccgagctcg ttacccagct cgtaaacaag atcctcatcg gtggcaagaa gtccaccgca      1140
gagcgcatcg tctacggtgc actcgagatc tgccgtgaga agaccggcac cgatccagta      1200
ggaaccctcg agaaggctct cggcaacgtg cgtccagacc tcgaagttcg ttcccgccgt      1260
gttggtggcg ctacctacca ggtgccagtg gatgttcgcc cagagcgcgc aaacaccctc      1320
gcactgcgtt ggttggtaac cttcacccgt cagcgtcgtg agaacaccat gatcgagcgt      1380
cttgcaaacg aacttctgga tgcagccaac ggccttggcg cttccgtgaa gcgtcgcgaa      1440
gacacccaca agatggcaga ggccaaccgc gccttcgctc actaccgctg gtagtactgc      1500
caagacatga aagcccaatc acctttaaga tcaacgcctg ccggcgccct tcacatttga      1560
ataagctggc agcctgcgtt tcttcaaggc gactgggctt ttagtctcat taatgcagtt      1620
caccgctgta agatagctaa atagaaacac tgtttcggca gtgtgttact aaaaaatcca      1680
tgtcacttgc ctcgagcgtg ctgcttgaat cgcaagttag tggcaaaatg taacaagaga      1740
attatccgta ggtgacaaac ttttttaatac ttgggtatct gtcatggata ccccggtaat     1800
aaataagtga attaccgtaa ccaacaagtt ggggtaccac tgtggcacaa gaagtgctta     1860
aggatctaaa caaggtccgc aacatcggca tcatggcgca catcgatgct ggtaagacca     1920
cgacca                                                                1926
```

<210> SEQ ID NO 9
<211> LENGTH: 1594
<212> TYPE: DNA
<213> ORGANISM: Artificial sequence

```
<220> FEATURE:
<223> OTHER INFORMATION: Synthetic DNA
<221> NAME/KEY: allele
<222> LOCATION: (659)..(1039)
<223> OTHER INFORMATION: rpsL-1545 allele
<221> NAME/KEY: mutation
<222> LOCATION: (86)..(86)
<223> OTHER INFORMATION: a to g

<400> SEQUENCE: 9
gatctagagg ttgccggtaa tcctgttgcg gacaatattt acaggatctg acacattggg      60
catcgctggg ggagtggtct cgtaggccgc cggcgcatag gaggcgccgg gaaattgctg     120
accaagcaga gtgtagggat tgtcgttcac atcagagatc agctctacaa gagtgtctaa     180
gtggcgggca ttccatgctt tggaggagcg atcttcaaat tcctccaaag tgagttgacc     240
tcgggaaaca gctgcagaaa gttcatccac gacttggttt cggttaaggt cagtggcgag     300
cttctttgct ggttcgtttc cttgaggaac agtcatggga accattctaa caagggattt     360
ggtgttttct gcggctagct gataatgtga acggctgagt cccactcttg tagttgggaa     420
ttgacggcac ctcgcactca agcgcggtat cgcccctggt tttccgggac gcggtggcgc     480
atgtttgcat ttgatgaggt tgtccgtgac atgtttggtc gggccccaaa aagagccccc     540
ttttttgcgt gtctggacac tttttcaaat ccttcgccat cgacaagctc agccttcgtg     600
ttcgtccccc gggcgtcacg tcagcagtta agaacaact ccgaaataag gatgttcat      660
gccaactatt cagcagctgg tccgtaaggg ccgccacgat aagtccgcca aggtggctac     720
cgcggcactg aagggttccc ctcagcgtcg tggcgtatgc acccgtgtgt acaccaccac     780
ccctaggaag cctaactctg ctcttcgtaa ggtcgctcgt gtgcgcctta cctccggcat     840
cgaggtttcc gcttacatcc ctggtgaggg ccacaacctg caggagcact ccatggtgct     900
cgttcgcggt ggtcgtgtta aggacctccc aggtgtccgt tacaagatcg tccgtggcgc     960
actggatacc caggtgtta aggaccgcaa gcaggctcgt tccccgctac ggcgcgaaga    1020
ggggataatt aaaaatgcgt aaatcagcag ctcctaagcg tccagtagtt caggaccctg    1080
tatacaagtc cgagctcgtt acccagctcg taaacaagat cctcatcggt ggcaagaagt    1140
ccaccgcaga gcgcatcgtc tacggtgcac tcgagatctg ccgtgagaag accggcaccg    1200
atccagtagg aaccctcgag aaggctctcg caacgtgcg tccagacctc gaagttcgtt     1260
cccgccgtgt tggtggcgct acctaccagg tgccagtgga tgttcgccca gagcgcgcaa    1320
acaccctcgc actgcgttgg ttggtaacct tcacccgtca gcgtcgtgag aacaccatga    1380
tcgagcgtct tgcaaacgaa cttctggatg cagccaacgg ccttggcgct tccgtgaagc    1440
gtcgcgaaga cacccacaag atggcagagg ccaaccgcgc cttcgctcac taccgctggt    1500
agtactgcca agacatgaaa gcccaatcac ctttaagatc aacgcctgcc ggcgcccttc    1560
acatttgaat aagctggcag cctgcgtcta gatc                               1594

<210> SEQ ID NO 10
<211> LENGTH: 20
<212> TYPE: DNA
<213> ORGANISM: Artificial sequence
<220> FEATURE:
<223> OTHER INFORMATION: Synthetic DNA

<400> SEQUENCE: 10
cagctctaca agagtgtcta                                                 20
```

```
<210> SEQ ID NO 11
<211> LENGTH: 20
<212> TYPE: DNA
<213> ORGANISM: Corynebacterium glutamicum

<400> SEQUENCE: 11
tggtcgtggt cttaccagca                                              20

<210> SEQ ID NO 12
<211> LENGTH: 28
<212> TYPE: DNA
<213> ORGANISM: Artificial sequence
<220> FEATURE:
<223> OTHER INFORMATION: Synthetic DNA

<400> SEQUENCE: 12
gatctagagg ttgccggtaa tcctgttg                                     28

<210> SEQ ID NO 13
<211> LENGTH: 28
<212> TYPE: DNA
<213> ORGANISM: Artificial sequence
<220> FEATURE:
<223> OTHER INFORMATION: Synthetic DNA

<400> SEQUENCE: 13
gatctagacg caggctgcca gcttattc                                     28

<210> SEQ ID NO 14
<211> LENGTH: 20
<212> TYPE: DNA
<213> ORGANISM: Corynebacterium glutamicum

<400> SEQUENCE: 14
atgaggttgt ccgtgacatg                                              20
```